United States Patent
Fang et al.

(10) Patent No.: US 9,518,151 B2
(45) Date of Patent: Dec. 13, 2016

(54) LOW DIELECTRIC CONSTANT POLYMER CONTAINING DINAPHTHYL AND HEXAFLUOROCYCLOBUTYL ETHER UNIT, PREPARATION METHOD AND USE

(71) Applicant: SHANGHAI INSTITUTE OF ORGANIC CHEMISTRY, CHINESE ACADEMY OF SCIENCES, Shanghai (CN)

(72) Inventors: Qiang Fang, Shanghai (CN); Chao Yuan, Shanghai (CN); Kaikai Jin, Shanghai (CN); Yingchun Liu, Shanghai (CN); Shen Diao, Shanghai (CN); Kai Li, Shanghai (CN)

(73) Assignee: Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 14/785,522

(22) PCT Filed: Nov. 20, 2013

(86) PCT No.: PCT/CN2013/087543
§ 371 (c)(1),
(2) Date: Oct. 19, 2015

(87) PCT Pub. No.: WO2014/169651
PCT Pub. Date: Oct. 23, 2014

(65) Prior Publication Data
US 2016/0060394 A1    Mar. 3, 2016

(30) Foreign Application Priority Data

Apr. 19, 2013  (CN) .......................... 2013 1 0138980

(51) Int. Cl.
| | |
|---|---|
| C08G 65/38 | (2006.01) |
| C08G 65/40 | (2006.01) |
| C07C 41/30 | (2006.01) |
| C08G 61/12 | (2006.01) |
| H01L 51/05 | (2006.01) |
| C07C 41/16 | (2006.01) |
| C07C 41/24 | (2006.01) |
| C07C 41/09 | (2006.01) |
| C07C 43/247 | (2006.01) |
| C09D 171/12 | (2006.01) |
| C08G 2/00 | (2006.01) |

(52) U.S. Cl.
CPC .............. *C08G 65/40* (2013.01); *C07C 41/09* (2013.01); *C07C 41/16* (2013.01); *C07C 41/24* (2013.01); *C07C 41/30* (2013.01); *C07C 43/247* (2013.01); *C08G 61/12* (2013.01); *C09D 171/12* (2013.01); *H01L 51/052* (2013.01); *C07C 2101/04* (2013.01); *C08G 2261/146* (2013.01); *C08G 2261/344* (2013.01); *C08G 2261/43* (2013.01); *C08G 2261/65* (2013.01)

(58) Field of Classification Search
CPC ................................ C08G 65/40; C07C 41/09
USPC ...... 525/242, 292, 326.2; 526/120, 192, 204, 526/247, 242, 270, 320; 528/219
See application file for complete search history.

(56) References Cited

U.S. PATENT DOCUMENTS 5,037,917 A * 8/1991 Babb ..................... C07C 17/269
526/242

FOREIGN PATENT DOCUMENTS

| CN | 101445511 | 6/2009 |
| WO | 90/15043 | 12/1990 |

OTHER PUBLICATIONS

J. Zhou et al., "Formation and Characterization of Perfluorocyclobutyl Polymer Thin Films," Journal of Applied Polymer Science, (2013), p. 3226-3236.
International Search Report for international application No. PCT/CN2013/087543, dated Feb. 27, 2014 (8 pages).
S. T. Iacono et al., "Facile preparation of fluorovinylene aryl ether telechelic polymers with dual functionality for thermal chain extension and tandem crosslinking," Chem. Commun., (2006) p. 4844-4846.
K. Lei et al., "Synthesis and Characterization of Novel Polymers Containing Perfluorocyclobutyl," Insulating Materials, vol. 44, No. 5 (2011), p. 11-16 with English abstract and cited in PCT International Search Report.
K. Tsuchiya et al., "Synthesis of a Novel Poly (binaphthylene ether) with a Low Dielectric Constant," Macromolecules, vol. 37 (2004), p. 4794-4797.
K. Tsuchiya et al., "Synthesis of a Novel Poly (binaphthylene ether) Containing Trifluoromethyl Groups with a Low Dielectric Constant," Macromolecules, vol. 39 (2006), p. 3964-3966.
C. Yuan et al., "Non-Porous Low-k Dielectric Films Based on a New Structural Amorphous Fluoropolymer," Advanced Materials, vol. 25 (2013), p. 4875-4878.

* cited by examiner

*Primary Examiner* — Terressa Boykin
(74) *Attorney, Agent, or Firm* — Hamre, Schumann, Mueller & Larson, P.C.

(57) ABSTRACT

The present invention belongs to the field of preparation of high performance polymers, and specifically relates to a low dielectric constant polymer containing dinaphthyl and hexafluorocyclobutyl ether units, and preparation method and use thereof. The polymer is prepared as follows: under the effect of an alkali, 1-naphthol bromotetrafluoroethane ether is prepared from 1-naphthol and tetrafluorodibromoethane in an organic solvent, and then reduced by a zinc powder so as to obtain 1-naphthol trifluorovinyl ether. 1-naphthol trifluorovinyl ether is treated at a high temperature to obtain a bisnaphthol hexafluorocyclobutyl ether monomer. The monomer is subjected to oxidative coupling in the presence of ferric trichloride so as to obtain a thermal polymer containing dinaphthyl and hexafluorocyclobutyl structural units with a good film-forming property, and in a nitrogen atmosphere, the temperature for 5% weight loss ($T_{d5\%}$) of the obtained film is 437° C., and the carbon residue yield at 1000° C. is 54.24%. The dielectric constant (30 MHz) of the film is 2.33. The polymer is suitable for use in the electronic and electrical industries as an insulation coating layer and an encapsulating material for electron components.

15 Claims, 1 Drawing Sheet

SEM

LOW DIELECTRIC CONSTANT POLYMER CONTAINING DINAPHTHYL AND HEXAFLUOROCYCLOBUTYL ETHER UNIT, PREPARATION METHOD AND USE

TECHNICAL FIELD

The present invention belongs to the field of preparation of high-performance polymers, and particularly relates to a polymer which contains dinaphthyl and hexafluorocyclobutyl ether units and has superior mechanical properties, low water absorption and low dielectric constant, and to a preparation method thereof.

BACKGROUND OF THE INVENTION

Polynaphthalene was studied since the 1960s because of its excellent heat resistance and optical performance. So far, as organic electroluminescent materials and lithium ion secondary battery materials, they have been widely used in the field of functional organic photoelectric materials. Meanwhile, polyethylene naphthalate which is produced from precursor of naphthalene dicarboxylic acid has been used as a unique polymer material alternative to glass in carbonated drinks and beer packaging industry due to its excellent gas barrier properties.

From 1990s, with the development of microelectronics industry, 90-nanometer chip manufacturing industry based on copper interconnection technology has made many demands for the material industry, among which the most urgent one is a material having both low dielectric constant and high heat resistance quality. Dow Company had developed several low dielectric materials. In addition to the famous SILK, a silicon-containing benzocyclobutene was developed. The oligomers which are obtained after prepolymerization treatment of these materials have good film-forming properties. After further curing with heating, solid films with dielectric constant up to 2.5 can be obtained. However, these materials are expensive, so it is necessary to develop inexpensive materials. Since the outstanding characteristics of polynaphthalate, Ueda et al. in Japan developed binaphthyl ether polymers (see *Macromolecules* 2004, 37, 4794 and *Macromolecules* 2006, 39, 3964). These materials have outstanding heat resistance qualities and are inexpensive. However, the dielectric constants of these materials are greater than 2.5, so the electrical properties are inferior to those of Dow's products.

It is known that the fluorine-containing polyaryl ethers have low dielectric constant and high heat resistance. However, the synthesis of fluorine-containing polyaryl ether involves using expensive perfluoro-benzene, thus greatly increasing cost of materials. In recent years, polyperfluorocyclobutane (PFCB) polymers from tetrafluoroethylene attract high attention from people, because these polymers have not only relatively low cost, but also high temperature resistance quality, chemical stability, excellent electrical properties, low moisture absorption and good mechanical properties (see WO9015043). However, since the [2+2] cycloaddition reactions occur at high temperatures of trifluoromethyl vinyl ether, which is a precursor of perfluorocyclobutane, usually tend to be incomplete, the heat resistance and dielectric properties of film are unstable. It should be particularly noted that such polymers often contain unreacted trifluoromethyl vinyl ether end groups, which are susceptible to attack from nucleophilic reagents, so that they are defluorinated, thereby lowering performance of materials (see *Chem. Commun.*, 2006, 4844-4846).

Summing up, there is an urgent need in the art to develop a polymer material of low-cost, good electrical properties, and stability to heating.

SUMMARY OF THE INVENTION

A purpose of the present invention is to provide a polymer comprising dinaphthyl and hexafluorocyclobutyl ether units, and the preparation processes and application thereof. The polymer of the present invention is of excellent performance, and can be used in microelectronics industry and large motor manufacturing industry as low dielectric materials or external coating insulating materials of metal wire.

In the first aspect of the present invention, it provides a low dielectric constant polymer comprising dinaphthyl and hexafluorocyclobutyl ether units, the polymer has a chemical structure of formula B:

Formula B

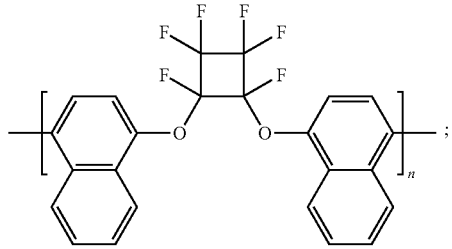

wherein n=5 to 200.

In a preferred embodiment, the number-average molecular weight of the polymer is 2,250 to 90,000.

In the second aspect of the present invention, it provides a preparing process of a polymer containing dinaphthyl and hexafluorocyclobutyl ether units in the first aspect of the invention, wherein it comprises the following steps: in an organic solvent and in presence of a ferric salt, conducting an oxidative polymerization reaction using binaphthol-hexafluorocyclobutyl ether as a raw material, thereby producing the polymer;

wherein the binaphthol-hexafluorocyclobutyl ether has the following structure:

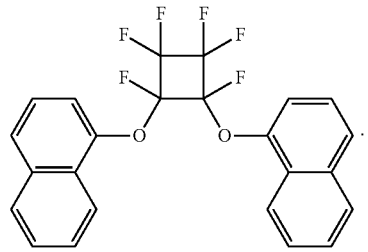 [SMILES: FC1(F)C(F)(F)C(F)(Oc2cccc3ccccc23)C1(F)Oc1cccc2ccccc12]

In a preferred embodiment, the ferric salt is selected from ferric chloride, ferric bromide, ferric sulfate, ferric nitrate, or combination thereof.

In a preferred embodiment, the ferric salt is ferric chloride.

In a preferred embodiment, the molar ratio between the raw material of binaphthol-hexafluorocyclobutyl ether and the ferric salt is 1:1-10.

In a preferred embodiment, the molar ratio between the raw material of binaphthol-hexafluorocyclobutyl ether and the ferric salt is 1:2-5.

In a preferred embodiment, the organic solvent is selected from nitrobenzene, dichloromethane, dichloroethane, tetrachloroethane, chlorobenzene or dichlorobenzene.

In a preferred embodiment, the organic solvent is tetrachloroethane.

In a preferred embodiment, the polymerization reaction temperature is −50 to 30° C., preferably −30° C. to 10° C.

In a preferred embodiment, the polymerization reaction time is 5 to 48 hrs.

In a preferred embodiment, in the preparation method, the raw material of binaphthol-hexafluorocyclobutyl ether is prepared a method comprising the following steps:
(1) in presence of potassium carbonate or potassium hydroxide and in N-methylpyrrolidone or DMSO solvent, reacting 1-naphthol and tetrafluorodibromoethane at room temperature for 10 to 20 hours, thereby forming 1-naphthyl-bromo tetrafluoroethane ether; wherein the molar ratio between 1-naphthol and tetrafluorodibromoethane is 1:1-10;
(2) in refluxing acetonitrile and in presence of zinc, conducting an elimination reaction of 1-naphthyl-bromotrifluoroethane ether for 5 to 20 hours, thereby forming 1-naphthyl-trifluorovinyl ether; wherein the molar ratio of 1-naphthyl-bromotrifluoroethane ether and zinc is 1:1-5;
(3) at a high temperature of 150 to 250° C., conducting a [2+2] cyclization reaction of 1-naphthyl-trifluorovinyl ether for 5 to 15 hours, thereby forming binaphthol-hexafluorocyclobutyl ether.

In the third aspect of the present invention, it provides a use of the polymer comprising dinaphthyl and hexafluorocyclobutyl ether units in the first aspect of the present invention in preparation of low dielectric materials or external coating insulating materials for metal wire.

In a preferred embodiment, the polymer is processed by hot molding or by dissolving the polymer with an organic solvent to form a solution and spin coating or drop coating, thereby obtaining a polymer sheet or film.

In a preferred embodiment, the organic solvent is selected from the group consisting of toluene, xylene, trimethylbenzene, diphenyl ether, cyclohexanone, chloroform, acetone, N,N-dimethylformamide, N,N-dimethylacetamide, dimethylsulfoxide, N-methyl pyrrolidone, or combination thereof.

In the fourth aspect of the present invention, it provides a compound of formula A:

Formula A

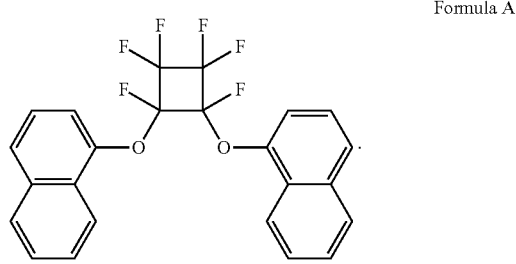 [SMILES: FC1(F)C(F)(F)C(F)(Oc2cccc3ccccc23)C1(F)Oc1cccc2ccccc12]

In the fifth aspect of the present invention, it provides a preparation method of compound of formula A in the fourth aspect of the present invention, which comprises the following steps:
(1) in presence of potassium carbonate or potassium hydroxide, in N-methylpyrrolidone or DMSO solvent, reacting 1-naphthol and tetrafluorodibromoethane at room temperature for 10 to 20 hours, thereby forming 1-naphthyl-bromotetrafluoroethane ether; wherein the molar ratio between 1-naphthol and tetrafluorodibromoethane is 1:1-10;
(2) in refluxing acetonitrile and in presence of zinc, conducting an elimination reaction of 1-naphthyl-bromotrifluoroethane ether for 5 to 20 hours, thereby forming 1-naphthyl-trifluorovinyl ether; wherein the molar ratio of 1-naphthyl-bromotrifluoroethane ether and zinc is 1: 1-5;
(3) at a high temperature of 150 to 250° C., conducting a [2+2] cyclization reaction of 1-naphthyl-trifluorovinyl ether for 5 to 15 hours, thereby forming binaphthol-hexafluorocyclobutyl ether.

In the sixth aspect of the present invention, it provides a polymer which is prepared by homopolymerizing or copolymerizing the compound in the fourth aspect of the present invention, or a polymer which comprises the compound in the fourth aspect of the present invention as a monomer.

In the seventh aspect of the present invention, it provides a product which is prepared with the polymer in the first aspect of the present invention or the sixth aspect of the present invention, or a product which comprises the compound in the first aspect of the present invention or the sixth aspect of the present invention.

In a preferred embodiment, the product is a low dielectric material or an external coating insulating material for metal wire.

In a preferred embodiment, the product is a film or a granule.

In a preferred embodiment, the film is prepared by any of the following methods: hot molding, spin coating, or drop coating.

In a preferred embodiment, the product possesses one or more of the following features:

Under a nitrogen atmosphere, the product has a 5% weight loss temperature ($T_{d5\%}$) of 400 to 480° C., preferably 420 to 450° C.;

The carbon residue yield at 1000° C. is 40% to 70%, preferably 50% to 60%.

In a preferred embodiment, the dielectric constant of the film (30 MHz) is 1~5, preferably 2~4.

In a preferred embodiment, the product is an insulating cover layer or an insulating spacer layer.

In a preferred embodiment, the product is packaging material for electronic components.

In the eighth aspect of the present invention, it provides a product which is prepared with the compound in the fourth aspect of the present invention, or a product which comprises the compound in the fourth aspect of the present invention.

In the ninth aspect of the present invention, it provides a use of compound of formula A wherein (1) the compound is used as a monomer of polymer, or is used for preparing a polymer of formula B; or (2) the compound is used for preparing a low dielectric material or an external coating insulating material for metal wire.

It should be understood that, in the present invention, each of the technical features specifically described above and below (such as those in the Examples) can be combined with each other, thereby constituting new or preferred technical solutions which need not be specified redundantly herein.

EMBODIMENTS FOR CARRYING OUT THE INVENTION

Figure 1:
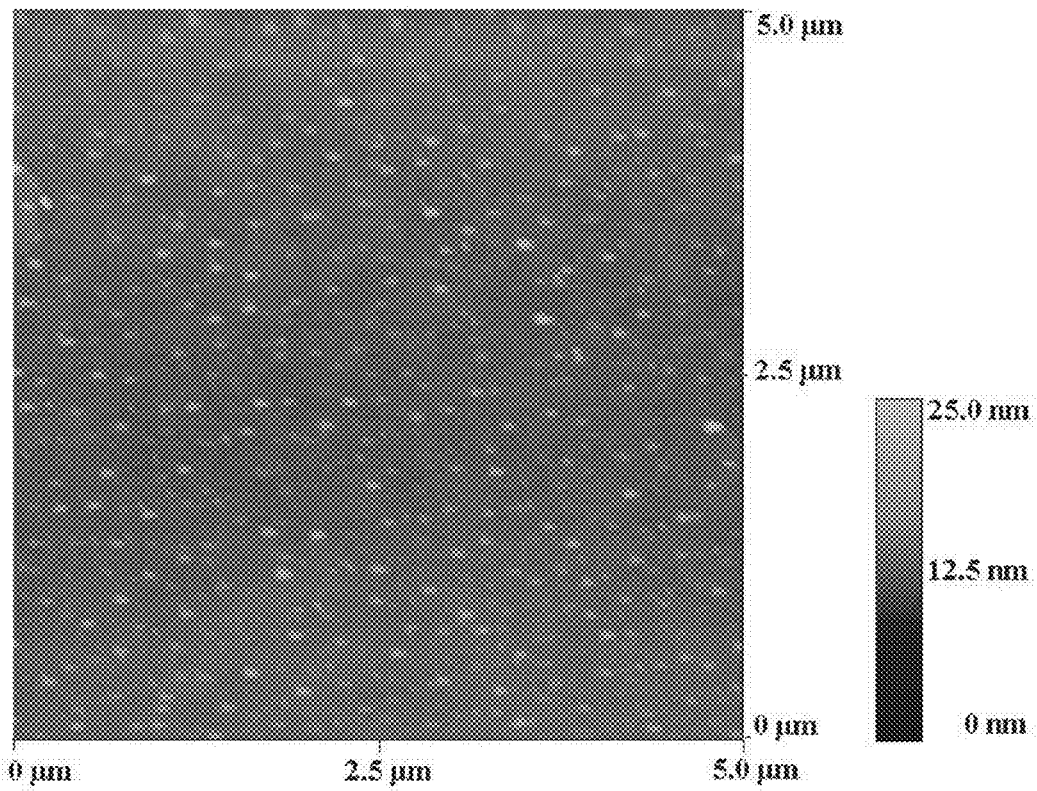
FIG. 1 shows the SEM graph of the polymer.

Through a long-term and intensive research, the inventors have unexpectedly discovered a new polymer monomer, of which the both ends are naphthyl, and the middle is hexafluorocyclobutyl ether functional group. A polymer having a novel structure is produced by directly connecting the naphthalene rings via an oxidative coupling method. The synthesis of this polymer is low-cost and simple. The polymer have excellent thermostability, low water absorption and low dielectric constant, and can be used as high-performance electronic packaging materials or outer coating layer for metal wire in the fields such as microelectronics industry and large motor manufacturing industry. The present invention is completed based on the above discovery.

Binaphthol-Hexafluorocyclobutyl Ether

The present invention provides a compound of formula A:

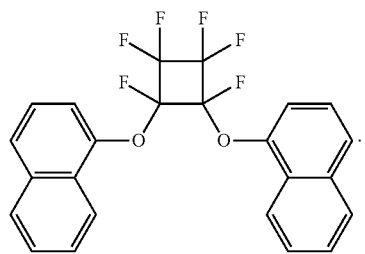

Formula A

The above compound can be used as a monomer of polymer to prepare a polymer comprising dinaphthyl and hexafluorocyclobutyl ether units.

Polymer Comprising Dinaphthyl and Hexafluorocyclobutyl Ether Units

The chemical structure of polymer comprising dinaphthyl and hexafluorocyclobutyl ether units of the present invention is as follows:

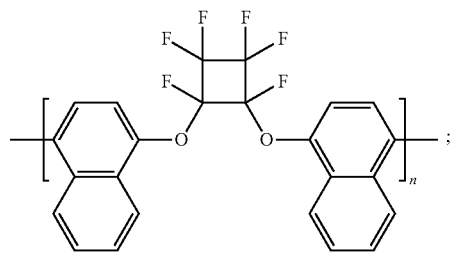

Formula B wherein n=5 to 200.

The number-average molecular weight of the polymer is 2,250 to 90,000.

The number-average molecular weight of another kind of preferred polymer is 10,000 to 300,000.

The weight-average molecular weight of another kind of preferred polymer is 10,000 to 400,000.

In another kind of preferred polymer, the degree of polymerization (n) is 10 to 500, 200 to 500, or 500 to 1000.

The polymer containing binaphthyl and hexafluorocyclobutyl ether units of the present invention can be prepared by using a common methods in the field, for example, by using the following steps: in an organic solvent and in presence of a ferric salt, conducting an oxidative polymerization reaction using binaphthol-hexafluorocyclobutyl ether as a raw material, thereby producing the polymer.

The ferric salt used in the preparation process of the polymer containing binaphthyl and hexafluorocyclobutyl ether units of the present invention is selected from ferric chloride, ferric bromide, ferric sulfate or ferric nitrate, and preferably ferric chloride.

In the preparation process of the polymer containing binaphthyl and hexafluorocyclobutyl ether units of the present invention, the molar ratio between the raw material of binaphthol-hexafluorocyclobutyl ether and ferric salt is 1:1-10, preferably 1:2-5.

The organic solvent used in the preparation process of the polymer containing binaphthyl and hexafluorocyclobutyl ether units of the present invention is selected from nitrobenzene, dichloromethane, dichloroethane, tetrachloroethane, chlorobenzene or dichlorobenzene. Preferably, it is tetrachloroethane.

The polymerization reaction temperature for producing the polymer containing binaphthyl and hexafluorocyclobutyl ether units of the present invention is −50 to 30° C., and preferably −30° C. to 10° C.

The polymerization reaction time for producing the polymer containing binaphthyl and hexafluorocyclobutyl ether units of the present invention is 5 to 48 hrs.

The raw material of binaphthol-hexafluorocyclobutyl ether, which is used in the preparation process of the polymer containing binaphthyl and hexafluorocyclobutyl ether units of the present invention, is prepared by a method comprising the following steps:

(1) in presence of potassium carbonate or potassium hydroxide and in N-methylpyrrolidone or DMSO solvent, reacting 1-naphthol and tetrafluorodibromoethane at room temperature for 10 to 20 hours, thereby forming 1-(2-bromo-1,1,2,2-tetrafluoro-ethoxy) naphthalene;

(2) in refluxing acetonitrile and in presence of zinc, conducting an elimination reaction of 1-(2-bromo-1,1,2,2-tetrafluoro-ethoxy) naphthalene, thereby forming 1-(1,2,2-trifluorovinyloxy)naphthalene;

(3) at a high temperature of 150 to 250° C., conducting a [2+2] cyclization reaction of 1-naphthyl-trifluorovinyl ether, thereby forming binaphthol-hexafluorocyclobutyl ether.

The polymer containing binaphthyl and hexafluorocyclobutyl ether units of the present invention can form a sheet by hot molding, or it can be formulated into a solution and then processed by spin coating or drop coating, thereby forming a polymer film. The solution used for spin coating or drop coating is obtained by dissolving the polymer in an organic solvent. The organic solvent is selected from the group consisting of toluene, xylene, trimethylbenzene, diphenyl ether, cyclohexanone, chloroform, acetone, N,N-dimethylformamide, N,N-dimethylacetamide, dimethylsulfoxide, N-methyl pyrrolidone, or combination thereof.

The polymer containing binaphthyl and hexafluorocyclobutyl ether units and produced according to the present invention possesses outstanding properties. It can be used in electronic and electrical industry, as an insulating cover layer and a packaging material for electronic components. In a preferred embodiment, the resultant polymer possesses good film-forming property, while under a nitrogen atmosphere, the 5% weight loss temperature ($T_{d5\%}$) of the film obtained is 437° C., and the carbon residue yield at 1000° C. is 54.24%. The dielectric constant of the film (30 MHz) is 2.33.

The main advantages of the present invention include the following ones:

(1) A structurally novel monomer of polymer containing binaphthyl and hexafluorocyclobutyl ether units is prepared.

(2) A polymer containing binaphthyl and hexafluorocyclobutyl ether units is prepared. Said polymer has low dielectric constant, good film-forming property, excellent thermal stability, and low water absorption and, therefore, it is very suitable for preparing an insulating layer or a thermal insulating layer in a product.

(3) The polymer of the present invention uses an inexpensive raw material and is easy to prepare, thus suitable for industrial production.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

EXAMPLE 1

Preparation of Precursor 1:
1-(2-bromo-1,1,2,2-tetrafluoro-ethoxy)naphthalene

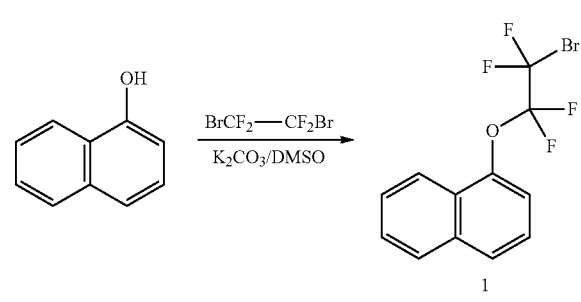

Under protection of argon, 57.6 g of 1-naphthol, 156 g of 1,2-dibromotetrafluoroethane and 350 ml currently distilled DMSO (dimethylsulfoxide) were added into a reaction apparatus and stirred for 30 minutes in an ice-water bath. Then 83 g of anhydrous potassium carbonate was added, the ice-water bath was removed, and the reaction was conducted for 6 hours at room temperature. The reaction mixture was poured into water, stirred vigorously for 20 minutes, and the product was extracted with chloroform in batches. The extract was washed with saturated aqueous sodium chloride solution, and then the chloroform was removed by rotary evaporation. The concentrate was rectificated, and the component at 65° C./0.23 mmHg was collected to obtain the product (106 g, yield 82%). Atmospheric boiling point was 254 to 255° C., H-NMR Characterization ($^1$H NMR, 300 MHz, CDCl$_3$, δ in ppm): 8.09~8.22(dd, 1H), 7.70~7.92(m, 2H), 7.50~7.68(m, 3H), 7.45(d, 1H); F-NMR Characterization ($^{19}$F NMR, 282 MHz, CDCl$_3$, δ in ppm): −84.8, (dt, 2F) −67.7(dt, 2F).

EXAMPLE 2

Preparation of Precursor 1:
1-(2-bromo-1,1,2,2-tetrafluoro-ethoxy)naphthalene

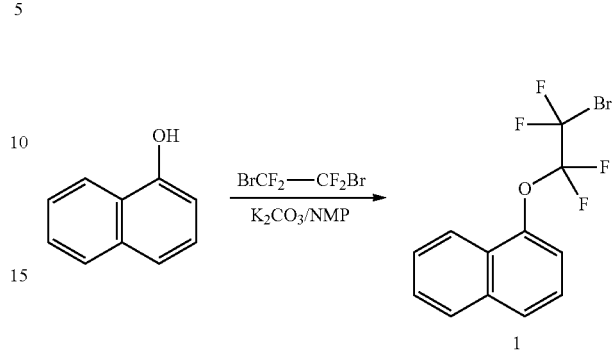

Under protection of argon, 57.6 g of 1-naphthol, 156 g of 1,2-dibromotetrafluoroethane and 350 ml currently distilled N-methylpyrrolidone (NMP) were added into a reaction apparatus and stirred for 30 minutes in an ice-water bath. Then 33.6 g of potassium hydroxide was added, the ice-water bath was removed, and the reaction was conducted for 6 hours at room temperature. The reaction mixture was poured into water, stirred vigorously for 20 minutes, and the product was extracted with chloroform in batches. The extract was washed with saturated aqueous sodium chloride solution, and then the chloroform was removed by rotary evaporation. The concentrate was rectificated, and the component at 65° C./0.23 mmHg was collected to obtain the product (85 g, yield 66%). Atmospheric boiling point was 254 to 255° C. H-NMR Characterization ($^1$H NMR, 300 MHz, CDCl$_3$, δ in ppm): 8.09~8.22 (dd, 1H), 7.70~7.92(m, 2H), 7.50~7.68(m, 3H), 7.45(d, 1H); F-NMR Characterization ($^{19}$F NMR, 282 MHz, CDCl$_3$, δ in ppm): −84.8, (dt, 2F) −67.7(dt, 2F).

EXAMPLE 3

Preparation of Precursor 2:
1-(1,2,2-trifluorovinyloxy)naphthalene

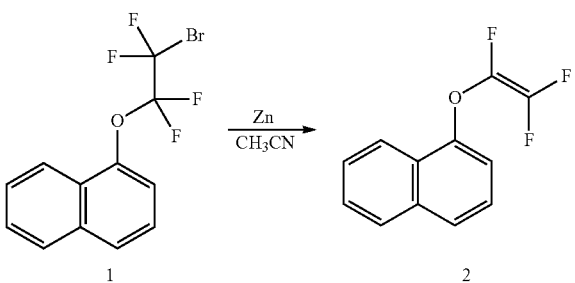

Under protection of argon, 65 g of 1-(2-bromo-1,1,2,2-tetrafluoro-ethoxy)naphthalene and 300 ml of currently distilled acetonitrile were added into a reaction bulb, stirred to dilute, and 28 g of zinc powder was added. The mixture was heated to react under refluxing for 24 hrs. The reaction mixture was poured into 600 ml of water, stirred for over 15 minutes, and the product was extracted with chloroform in batches. The chloroform extracts were combined and washed with saturated aqueous sodium chloride solution, and dried with anhydrous sodium sulfate for over 12 hrs. The chloroform was removed by rotary evaporation. The concentrate was rectificated, and the component at 62.7° C./0.6 mmHg was collected to obtain the product (34.5 g, yield 77%). Atmospheric boiling point was 242~243° C., H-NMR Characterization ($^1$H NMR, 300 MHz, CDCl$_3$, δ in ppm): 8.33(m, 1H), 7.94(m, 1H), 7.74(d, 1H), 7.64(m, 2H), 7.49 (m, 1H), 7.22(d, 1H); F-NMR Characterization ($^{19}$F NMR, 282 MHz, CDCl$_3$, δ in ppm): −133.6~−134.0(dd, 1F), −126.3~−126.6(dd, 1F), −119.4~−119.8(dd, 1F).

EXAMPLE 4

Preparation of Precursor 2:
1-(1,2,2-trifluorovinyloxy)naphthalene

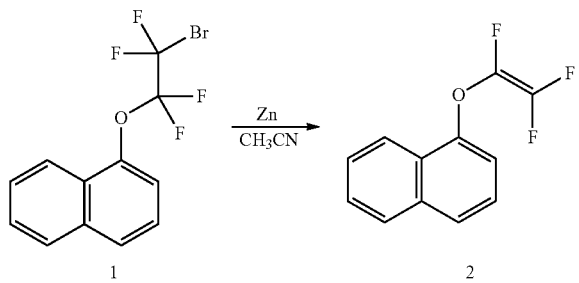

Under protection of argon, 65 g of 1-(2-bromo-1,1,2,2-tetrafluoro-ethoxy)naphthalene and 300 ml of currently distilled acetonitrile were added into a reaction bulb, stirred to dilute, and 40 g of zinc powder was added. The mixture was heated to react under refluxing for 24 hrs. The reaction mixture was poured into 1000 ml of water, stirred for over 15 minutes, and the product was extracted with chloroform in batches. The chloroform extracts were combined and washed with saturated aqueous sodium chloride solution, and dried with anhydrous sodium sulfate for over 12 hrs. The chloroform was removed by rotary evaporation. The concentrate was rectificated, and the component at 62.7° C./0.6 mmHg was collected to obtain the product (30 g, yield 67%). Atmospheric boiling point was 242~243° C. H-NMR Characterization ($^1$H NMR, 300 MHz, CDCl$_3$, δ in ppm): 8.33(m, 1H), 7.94(m, 1H), 7.74(d, 1H), 7.64(m, 2H), 7.49(m, 1H), 7.22(d, 1H); F-NMR Characterization ($^{19}$F NMR, 282 MHz, CDCl$_3$, δ in ppm): −133.6~−134.0(dd, 1F), −126.3~126.6 (dd, 1F), −119.4~119.8(dd, 1F).

EXAMPLE 5

Preparation of monomer of binaphthol-hexafluorocyclobutyl ether: 1,1'-(1,2,2,3,3,4,-hexafluoro cyclobutane-1,2-dioxy)-dinaphthalene

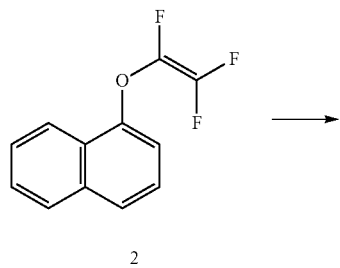

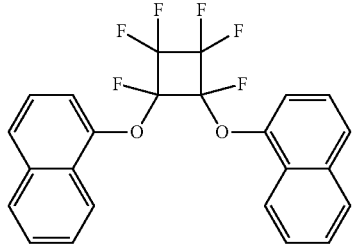

Under protection of argon, 23.2 g of 1-(1,2,2-trifluorovinyloxy)naphthalene and 50 ml of diphenyl ether were added into a reaction bulb, then heated to 150° C. to react for 24 hrs. After cooled to room temperature, a flash chromatography (petroleum ether/ethyl acetate, 10:1) and a recrystallization with isopropanol were was conducted to give the product (20.1 g, yield 86.6%). H-NMR Characterization ($^1$H NMR, 300 MHz, CDCl$_3$, δ in ppm): 8.29(d, 2H), 7.87(dd, 2H), 7.70(dd, 2H), 7.60(m, 4H), 7.38(m, 4H). F-NMR Characterization ($^{19}$F NMR, 282 MHz, CDCl$_3$, δ in ppm): −127.0~−131.4(m, 6F). Elemental analysis: calcd for C$_{24}$H$_{14}$F$_6$O$_2$: C, 64.29; H, 3.15; F, 25.42; O, 7.14. Found: C, 64.53; H, 3.09; F, 25.19; O, 7.19.

EXAMPLE 6

Preparation of monomer binaphthol-hexafluorocyclobutyl ether: 1,1'-(1,2,2,3,3,4,-hexafluorocyclobutane-1,2-dioxy)-dinaphthalene

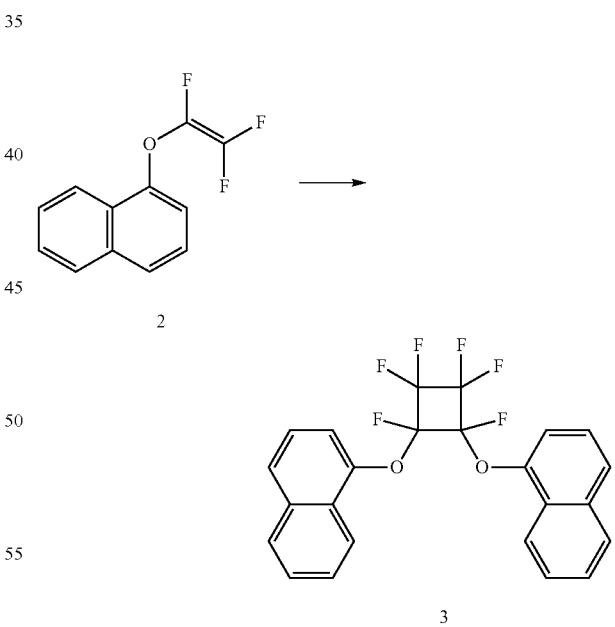

Under protection of argon, 23.2 g of 1-(1,2,2-trifluorovinyloxy)naphthalene and 50 ml of diphenyl ether were added into a reaction bulb, then heated to 200° C. to react for 24 hrs. After cooled to room temperature, a flash chromatography (petroleum ether/ethyl acetate, 10:1) and recrystallization with isopropanol was conducted to give the product (21 g, yield 89%). H-NMR Characterization ($^1$H NMR, 300 MHz, CDCl$_3$, δ in ppm): 8.29(d, 2H), 7.87(dd, 2H), 7.70(dd, 2H), 7.60(m, 4H), 7.38(m, 4H). F-NMR Characterization ($^{19}$F NMR, 282 MHz, CDCl$_3$, δ in ppm): −127.0~−131.4(m, 6F). Elemental analysis: calcd for C$_{24}$H$_{14}$F$_6$O$_2$: C, 64.29; H, 3.15; F, 25.42; O, 7.14. Found: C, 64.53; H, 3.09; F, 25.19; O, 7.19.

EXAMPLE 7

Preparation of Polymer

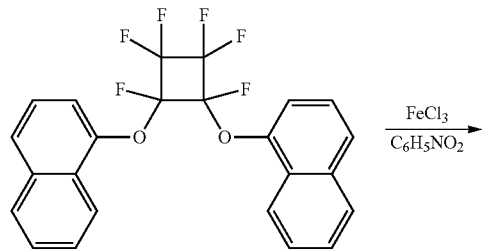

3

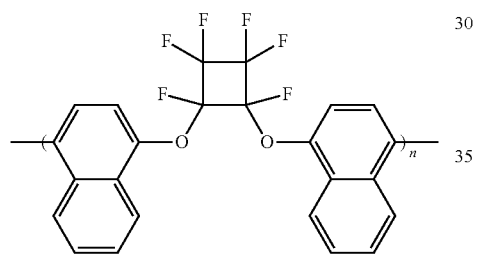

Under protection of argon, 15.7 g of monomer of binaphthol-hexafluorocyclobutyl ether, 17.1 g of anhydrous ferric chloride and 150 ml of nitrobenzene were added into a 100 ml three-necked bowling flask, stirred at room temperature for 30 mins, then heated to 35° C. under stirring to react for 8 hrs. After the reaction was completed, the reaction solution was poured into a large amount of methanol, and a small amount of concentrated hydrochloric acid was added for acidulation. It was stirred for 30 mins, and then stood, and the supernatant was decanted. The white solid was collected by suction filtration, and re-dissolved in about 40 ml of toluene, placed in a large amount of acetone for sedimentation, and allowed to stand, and the supernatant was decanted. The solid was collected by suction filtration, dried under vacuum at 200° C. for 12 hours and 15.3 g of polymer was obtained almost quantitatively. GPC test (Chloroform was used as an eluent. Polystyrene was used as a standard.) showed that the number-average molecular weight of the polymer was 4,200, and the weight-average molecular weight of the polymer was 8,300, and the polymerization degree of the polymer (n) was equivalent to 9. H-NMR Characterization ($^1$H NMR, 300 MHz, CDCl$_3$, δ in ppm): 8.46~8.26(d, 2H), 7.90~7.04(m, 12H). F-NMR Characterization ($^{19}$F NMR, 282 MHz, CDCl$_3$, δ in ppm): −126.4~−130.9(m, 6F). Elemental analysis: Calcd for C$_{24}$H$_{12}$F$_6$O$_2$: C, 64.57; H, 2.69; F, 25.56. Found: C, 64.28; H, 2.83; F, 25.37.

EXAMPLE 8

Preparation of Polymer

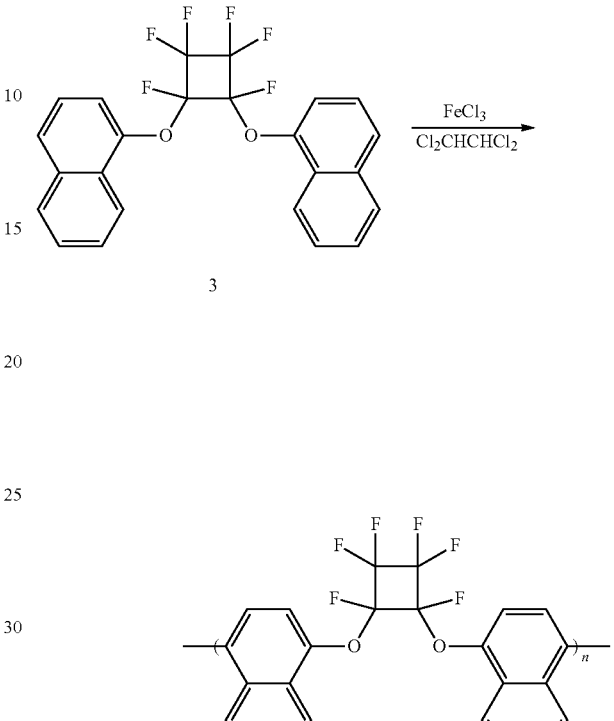

Under protection of argon, 15.7 g of monomer binaphthol-hexafluorocyclobutyl ethyl, 17.1 g of anhydrous ferric sulfate and 150 ml of tetrachloroethane were added into a 100 ml three-necked bowling flask, stirred at room temperature for 30 mins, then heated to 35° C. under stirring to react for 8 hrs. After the reaction was completed, the reaction solution was poured into a large amount of methanol, and a small amount of concentrated hydrochloric acid was added for acidulation. It was stirred for 30 mins, and then stood, and the supernatant was decanted. The white solid was collected by suction filtration, and re-dissolved in about 40 ml of toluene, placed in a large amount of acetone for sedimentation, and allowed to stand, and the supernatant was decanted. The solid was collected by suction filtration, dried under vacuum at 200° C. for 12 hours and 13 g of polymer was obtained. GPC test (Chloroform was used as an eluent. Polystyrene was used as a standard.) showed that the number-average molecular weight of the polymer was 90000, and the weight-average molecular weight of the polymer was 182,000, and the polymerization degree of the polymer (n) was equivalent to 200. H-NMR Characterization ($^1$H NMR, 300 MHz, CDCl$_3$, δ in ppm): 8.46~8.26(d, 2H), 7.90~7.04(m, 12H). F-NMR Characterization ($^{19}$F NMR, 282 MHz, CDCl$_3$, δ in ppm): −126.4~−130.9(m, 6F). Elemental analysis: Calcd for C$_{24}$H$_{12}$F$_6$O$_2$: C, 64.57; H, 2.69; F, 25.56. Found: C, 64.33; H, 2.91; F, 25.44.

EXAMPLE 9

Preparation of Polymer

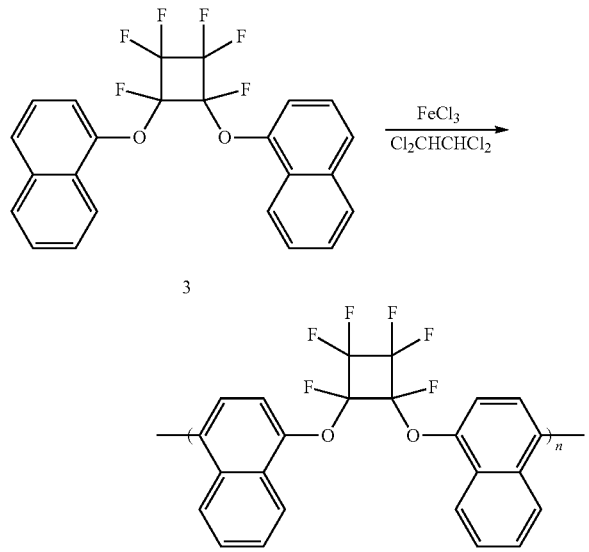

Under protection of argon, 15.7 g of monomer binaphthol-hexafluorocyclobutyl ethyl, 17.1 g of anhydrous ferric sulfate and 150 ml of tetrachloroethane were added into a 100 ml three-necked bowling flask, rapidly cooled to −30° C., and stirred under the same temperature to react for 8 hrs. After the reaction was completed, the reaction solution was poured into a large amount of methanol, and a small amount of concentrated hydrochloric acid was added for acidulation. It was stirred for 30 mins, and then stood, and the supernatant was decanted. The white solid was collected by suction filtration, and re-dissolved in about 20 ml of toluene, placed in a large amount of acetone for sedimentation, and allowed to stand, and the supernatant was decanted. The solid was collected by suction filtration, dried under vacuum at 200° C. for 12 hours and 15 g of polymer was obtained. GPC test (Chloroform was used as an eluent. Polystyrene was used as a standard.) showed that the number-average molecular weight of the polymer was 60000, and the weight-average molecular weight of the polymer was 121000, the polymerization degree of the polymer(n) was equivalent to 130. H-NMR Characterization ($^1$H NMR, 300 MHz, CDCl$_3$, δ in ppm): 8.46~8.26(d, 2H), 7.90~7.04(m, 12H). F-NMR Characterization ($^{19}$F NMR, 282 MHz, CDCl$_3$, δ in ppm): −126.4~−130.9(m, 6F). Elemental analysis: Calcd for $C_{24}H_{12}F_6O_2$: C, 64.57; H, 2.69; F, 25.56. Found: C, 64.45; H, 2.88; F, 25.62.

EXAMPLE 10

Purification of Polymer

In order to remove ferric ions probably contained in the polymer, it was necessary to purify the polymer. Otherwise, the dielectric properties of the polymer film will be greatly affected. Specifically, the purification steps were as follows:

5 g of each of the polymers prepared in Examples 7 to 9 was obtained, dissolved in 10 ml of toluene. The resultant solution was poured into a 40 cm length and 5 cm diameter glass column packed with 200 mesh neutral alumina. About 1000 ml of toluene was used for rinsing. The eluent was collected, concentrated to about 10 ml in volume, then settled in a large amount of acetone and allowed to stand. The supernatant was decanted and the solid was collected by suction filtration, and dried under vacuum at 200° C. for 12 hours. A white solid was obtained. ICP-MASS test showed that the iron content of the polymer was less than 1 ppm.

EXAMPLE 11

Thermal and Dielectric Properties of the Polymer

A polymer (0.5 g) obtained in Example 9 and purified in Example 10 was dissolved in 5 ml of toluene, and was spin-coated on a heavy doping silicon wafer (electrical resistivity 2×10$^{-3}$ Ω·cm), thus obtaining a thin polymer film with a thickness of 160 nm. The silicon wafer was put into a vacuum drying oven and heated for 2 hrs at 200° C. After cooled to room temperature in nitrogen, 1 mm aluminum electrode was deposited on the surface of the film, and 200 nm of aluminum was deposited on the back of the silicon wafer, thereby obtaining a standard film capacitors. The dielectric constant and dielectric loss factor of the film were calculated by testing capacitance of the film capacitor.

The film obtained by the above-described spin coating manner was placed in a closed vessel in which the relative humidity was 75%, and was placed at room temperature for a week. The water absorption of the film was calculated by measuring the weight change before and after the film was placed.

The film obtained by spin coating was crushed and placed in a thermal weight analyzer. The thermal decomposition temperature and carbon residue of the test polymer were tested by using a heating rate of 10° C./min.

The specific data were shown in the following table:

| 5% weight loss temperature (° C.) | Decomposing peak temperature (° C.) | Carbon residue yield (nitrogen, 1000° C.) | Water absorption | Dielectric constant (30 MHz) | Dielectric dissipation factor (30 MHz) |
|---|---|---|---|---|---|
| 437 | 454 | 54.2% | 0.12% | 2.33 | 1.21 × 10$^{-3}$ |

It can be seen from the above table that 5% weight loss temperature of the polymer was 437° C. When heated in nitrogen atmosphere to 1000° C., the carbon residue yield was 54.2%, indicating that the polymer had excellent thermal stability. It met the requirements of thermal stability of low dielectric constant materials in the field of industry. The water absorption of the polymer was 0.12%, indicating that it was of high hydrophobicity. Therefore it could avoid the degradation of material properties caused by moisture absorption, which met to the requirements of low k materials in integrated circuit industry. The dielectric constant of the polymer in 30 MHz was 2.33 and the dielectric loss factor was $1.21 \times 10^{-3}$. Compared to the reported low dielectric constant materials, the polymer had an extremely low dielectric constant, and therefore it was suitably useful as an LSI insulating material on the chip.

EXAMPLE 12

Figure 2:
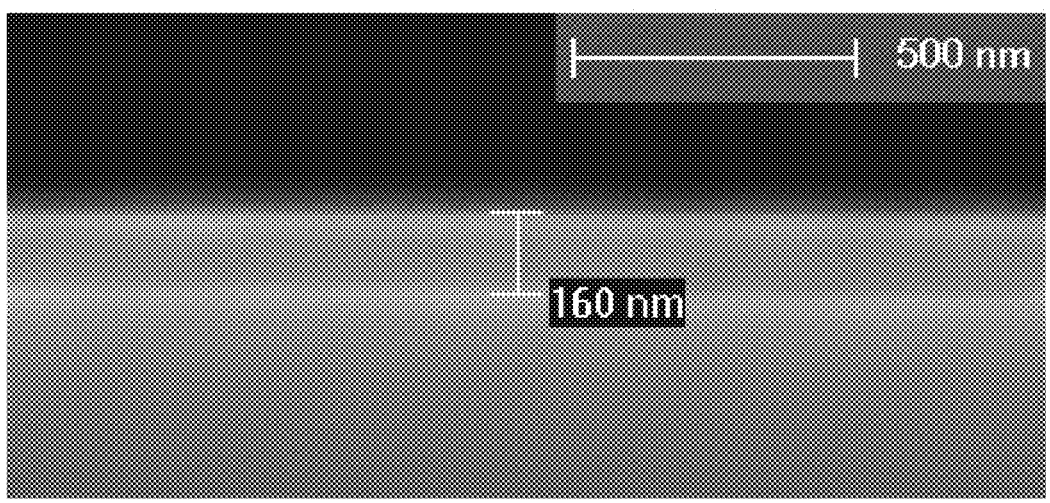
FIG. 2 shows the AFM graph of the polymer.

The polymer solution was spin-coated to the heavy doping silicon wafer to give a polymer film. It was shown by SEM and AFM studies (as shown in FIGS. 1 and 2) that, the thickness of the polymer film was 160 nm, and the surface roughness of the film was less than 6.7 nm within a 5 micrometer range, suggesting that the surface of the film was very uniform. The study of mechanical properties of the polymer by nano-indentation technique showed that the average hardness of the polymer film was 0.392 GPa, and the Young's modulus was 17.13 GPa. It indicated that it had good mechanical properties and met the requirements of LSI insulating materials.

The polymer designed in the present invention mainly can be used as high-performance insulating materials on LSI chips, and it can effectively reduce the capacitance resistance delay and crosstalk of IC. Further, it is possible to use is as a cladding layer of wire or cable in precision instruments. It has a dielectric constant reduced to 2.33 or less without introducing any porogen, and both thermal stability and mechanical properties can meet the requirements of applications in Damascus process.

In the present invention, the merits resulted from the non-necessity of introducing porogen are also shown in the following aspects:

First, it is no longer necessary to consider how to remove porogen (such as water, carbon dioxide, polystyrene, and the like). So the dielectric constant and dielectric loss would be infected simply by the designed structure.

Second, because the film prepared is a dense membrane, the mechanical properties of the film, such as Young's modulus and hardness, are maintained at a relatively high value.

Third, during the design process of the present invention, hydrogen peroxide is used to moderately oxidize in cooperation with hydrochloric acid before spin coating. Therefore, a certain amount of SiOH groups are generated on the surface, thus making the film have good adhesion properties to the treated silicon wafer due to the inherent polarity of the carbon-oxygen bonds in polyarylether.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A low dielectric constant polymer, comprising dinaphthyl hexafluorocyclobutyl ether units, the polymer having the following chemical structure:

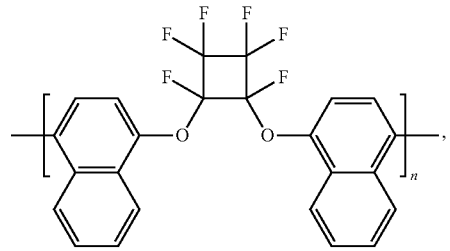

wherein n=5 to 200.

2. A process of preparing a polymer containing dinaphthyl hexafluorocyclobutyl ether units, comprising: in an organic solvent and in the presence of a ferric salt, conducting an oxidative polymerization reaction using binaphthol-hexafluorocyclobutyl ether as a raw material, thereby producing the polymer;
wherein the binaphthol-hexafluorocyclobutyl ether has the following structure:

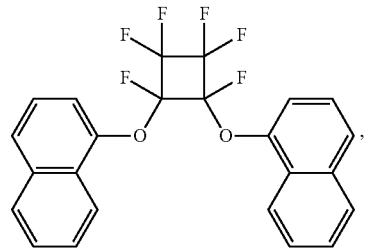 [SMILES: FC1(F)C(F)(F)C(F)(Oc2cccc3ccccc23)C1(F)Oc1cccc2ccccc12]

and
the polymer containing dinaphthyl hexafluorocyclobutyl ether units has the following chemical structure:

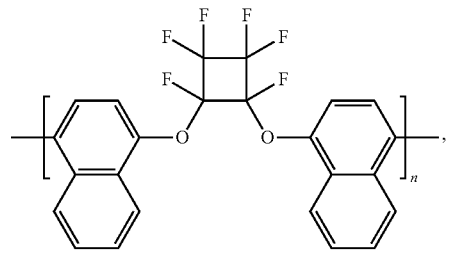

where n=5 to 200.

3. The process of claim 2, wherein the ferric salt is at least one selected from ferric chloride, ferric bromide, ferric sulfate or ferric nitrate, or combination thereof.

4. The process of claim 2, wherein the molar ratio between the raw material of binaphthol-hexafluorocyclobutyl ether and the ferric salt is 1:1-10.

5. The process of claim 2, wherein the organic solvent is at least one selected from nitrobenzene, dichloromethane, dichloroethane, tetrachloroethane, chlorobenzene or dichlorobenzene.

6. The process of claim 2, wherein the oxidative polymerization reaction is conducted at a temperature of −50 to 30° C.

7. The process of claim 2, wherein the oxidative polymerization reaction is conducted for 5 to 48 hrs.

8. A compound of formula A:

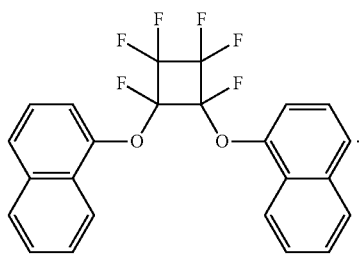 [SMILES: FC1(F)C(F)(F)C(F)(Oc2cccc3ccccc23)C1(F)Oc1cccc2ccccc12]

formula A

9. A preparation method of a compound of formula A, comprising:
(1) in the presence of potassium carbonate or potassium hydroxide and in N-methylpyrrolidone or DMSO solvent, reacting 1-naphthol and tetrafluorodibromoethane at room temperature for 10 to 20 hours, thereby forming 1-naphthyl-bromotetrafluoroethane ether, the molar ratio between 1-naphthol and tetrafluorodibromoethane being 1:1-10;
(2) in refluxing acetonitrile and in the presence of zinc, conducting an elimination reaction of the 1-naphthyl-bromotrifluoroethane ether for 5 to 20 hours, thereby forming 1-naphthyl-trifluorovinyl ether, the molar ratio of 1-naphthyl-bromotrifluoroethane ether and zinc being 1:1-5;
(3) at a high temperature of 150 to 250° C., conducting a [2+2] cyclization reaction of the 1-naphthyl-trifluorovinyl ether for 5 to 15 hours, thereby forming binaphthol-hexafluorocyclobutyl ether, wherein the compound of formula A is represented by

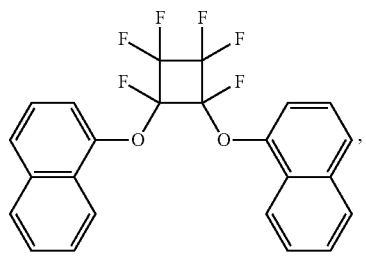

10. A film which comprises the low dielectric constant polymer of claim 1.

11. A granule comprising the low dielectric constant polymer of claim 1.

12. A material product used in industry comprising the low dielectric constant polymer of claim 1.

13. The material product used in industry of claim 12, wherein the material product used in industry is an external coating insulating material for metal wire.

14. The process of claim 2, wherein the oxidative polymerization reaction temperature is conducted at a temperature of −30° C. to 10° C.

15. A method for preparing a low dielectric material or an external coating insulating material using a compound of claim 8, comprising:
preparing a polymer of the compound of claim 8,
purifying the polymer.

* * * * *